(12) United States Patent
Stanton et al.

(10) Patent No.: US 12,181,053 B2
(45) Date of Patent: Dec. 31, 2024

(54) MEDICAL CLEANING VALVE

(71) Applicant: Boston Scientific Scimed, Inc., Maple Grove, MN (US)

(72) Inventors: Larry Stanton, Burlington, MA (US);
Allyn Jensrud, Milford, MA (US);
James Scutti, Norwell, MA (US);
Colby Harris, Norfolk, MA (US);
Robb Gavalis, Westborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/530,323

(22) Filed: Dec. 6, 2023

(65) Prior Publication Data

US 2024/0102560 A1    Mar. 28, 2024

Related U.S. Application Data

(63) Continuation of application No. 18/155,987, filed on Jan. 18, 2023, now Pat. No. 11,898,642, which is a
(Continued)

(51) Int. Cl.
*F16K 11/07* (2006.01)
*A61M 39/16* (2006.01)
(Continued)

(52) U.S. Cl.
CPC ......... *F16K 11/0712* (2013.01); *A61M 39/16* (2013.01); *F16K 11/0708* (2013.01);
(Continued)

(58) Field of Classification Search
CPC ...... F16K 31/445; F16K 31/44; F16K 35/025; F16K 35/022; F16K 35/027; F16K 11/0704; A61M 2039/224; A61M 2039/226

See application file for complete search history.

(56) References Cited

U.S. PATENT DOCUMENTS 4,537,209 A    8/1985 Sasa
5,027,791 A    7/1991 Takahashi
(Continued)

FOREIGN PATENT DOCUMENTS

CN      106667421 A    5/2017
WO    2015080694 A1    6/2015

OTHER PUBLICATIONS

International Search Report and Written Opinion of the International Search Authority dated Dec. 9, 2020, issued in International Application No. PCT/US2020/036825, filed Jun. 9, 2020 (14 pages).

*Primary Examiner* — Kelsey E Cary
(74) *Attorney, Agent, or Firm* — Seager, Tufte & Wickhem, LLP (57) ABSTRACT

A valve may have a fluid inlet and a fluid outlet. The valve may include a valve stem having a lumen extending from a first opening at a proximal portion of the valve stem to a second opening at a distal end of the valve stem. A plurality of seals may be positioned relative to the valve stem. The valve stem and seals may be configured so that a fluid entering the inlet is prevented from flowing to the outlet in a first position of the valve stem and relative to the inlet and the outlet. The valve stem and the seals may be configured so that a fluid entering the inlet flows to the outlet in a second position of the valve stem relative to the inlet and the outlet, the second position being more distal than the first position relative to the inlet and the outlet.

15 Claims, 3 Drawing Sheets

Related U.S. Application Data continuation of application No. 17/511,831, filed on Oct. 27, 2021, now Pat. No. 11,603,939, which is a continuation of application No. 16/896,971, filed on Jun. 9, 2020, now Pat. No. 11,187,329.

(60) Provisional application No. 62/859,537, filed on Jun. 10, 2019.

(51) Int. Cl.
  *F16K 31/44* (2006.01)
  *A61M 39/22* (2006.01)

(52) U.S. Cl.
  CPC .......... *F16K 11/0716* (2013.01); *F16K 31/44* (2013.01); *A61M 2039/224* (2013.01)

(56) References Cited

U.S. PATENT DOCUMENTS

| | | |
|---|---|---|
| 6,346,075 B1 | 2/2002 | Arai et al. |
| 10,441,826 B2 | 10/2019 | Dunn et al. |
| 2006/0213564 A1 | 9/2006 | Ricci et al. |
| 2015/0011831 A1 | 1/2015 | Ouchi |
| 2015/0083133 A1 | 3/2015 | Dunn et al. |
| 2015/0257634 A1 | 9/2015 | Nakade |
| 2016/0081538 A1 | 3/2016 | Rebholz et al. |
| 2018/0361034 A1 | 12/2018 | Tobien |

MEDICAL CLEANING VALVE

CROSS-REFERENCE TO RELATED APPLICATIONS

This application is a continuation of U.S. application Ser. No. 18/155,987, filed Jan. 18, 2023, which is a continuation of U.S. application Ser. No. 17/511,831, filed Oct. 27, 2021, and now U.S. Pat. No. 11,603,939, which is a continuation of U.S. application Ser. No. 16/896,971, filed Jun. 9, 2020, now U.S. Pat. No. 11,187,329, which claims the benefit of priority from U.S. Provisional Application No. 62/859,537, filed Jun. 10, 2019, each of which is incorporated by reference herein in its entirety.

TECHNICAL FIELD

The present disclosure relates generally to valves for medical devices, for example endoscopes.

BACKGROUND

Endoscopes include functionality to deliver fluids (including air and water) and suction to a site of a procedure. Tubing for delivering fluids and/or suction extends from a handle of the endoscope, through a sheath of the endoscope, and to a distal tip of the endoscope. During a procedure, body fluids, tissues, or other material could migrate into the tubing and, in some cases, lead to clogging of the tubing. In order to aid in reprocessing of reusable endoscopes between procedures, pre-processing is performed in an endoscopy suite. For example, water or other fluids are flushed through the tubing after the endoscope is removed from a patient, in order to clear debris from the air/water and/or suction tubing. One option for accomplishing such pre-processing is a reusable cleaning valve. Such cleaning valves may include a number of components, including a valve stem (often made of metal) with one or more channels therein, a number of seals, and an actuation mechanism. The cleaning valve may be inserted into an air/water valve cylinder of an endoscope after the scope is removed from a patient. An operator may then depress a button of the cleaning valve for a predetermined amount of time (e.g., 30 seconds) to flush the air and/or water channels of the endoscope prior to further reprocessing of the endoscope. A reusable cleaning valve must be subject to cleaning, itself, in between uses, which can add to reprocessing cost. Therefore, a need exists for valves capable of performing cleaning functions with less operator interaction or single use valves that do not need to themselves be processed.

SUMMARY

Embodiments of the present disclosure relate to, among other things, valves for medical devices. Each of the embodiments disclosed herein may include one or more of the features described in connection with any of the other disclosed embodiments.

According to one aspect, a valve for use in a medical device having a fluid inlet and a fluid outlet. The valve may include a valve stem having a lumen extending from a first opening at a proximal portion of a radially-outer surface of the valve stem to a second opening at a distal end of the valve stem; and a plurality of seals positioned relative to the valve stem. The valve stem and the plurality of seals may be configured so that a fluid entering the fluid inlet is prevented from flowing to the fluid outlet in a first position of the valve stem and the plurality of seals relative to the fluid inlet and the fluid outlet. Also, the valve stem and the plurality of seals may be configured so that a fluid entering the fluid inlet is flowable to the fluid outlet in a second position of the valve stem and the plurality of seals relative to the fluid inlet and the fluid outlet, the second position being more distal than the first position relative to the fluid inlet and the fluid outlet.

In other aspects of the present disclosure, the valve may include one or more of the features below. A channel seal may be at the second opening of the lumen. The channel seal may form a fluid-tight barrier over the second opening in the first position and may permit the flow of fluid through the second opening in the second position. The plurality of seals may be configured to form a slidable interference fit with a valve cylinder of the medical device so that a fluid is prevented from flowing between each of the plurality of seals and the wall of the valve cylinder. The lumen may include a bend proximate to the first opening. The channel seal may be configured to receive a channel stem. When the channel stem is positioned within the channel seal, the valve may be in the second position and fluid may flow between an area exterior to the valve stem, the second opening of the lumen, and the lumen. The valve may further include an actuation mechanism including a button and at least one biasing member, wherein the actuation mechanism is configured to transition the valve between the first position and the second position, and the valve is biased towards the first position. The actuation mechanism may be configured to align the first opening of the lumen with the fluid outlet when the valve is in the first position. The fluid inlet may be a first fluid inlet and the fluid outlet may be a first fluid outlet.

In other aspects of the present disclosure, the valve may include one or more of the features below. The medical device may further comprise a second fluid inlet and a second fluid outlet. The plurality of seals may include a first seal, a second seal, a third seal, and a fourth seal. The first seal may be positioned proximal to the first opening and proximal to the first fluid outlet when the valve is in the first position and when the valve is in the second position. The second seal may be positioned distal to the first opening and proximal to the first fluid outlet when the valve is in the first position. The second seal may be positioned distal to the first opening and distal to the first fluid outlet when the valve is in the second position. The third seal may be positioned distal to the second fluid inlet and proximal to the second fluid outlet when the valve is in the first position and when the valve is in the second position. The fourth seal may be positioned distal to the second fluid outlet and proximal to the first fluid inlet when the valve is in the first position and when the valve is in the second position. The lumen may be a first lumen, and the valve stem may further comprise a second lumen extending from a third opening at a distal portion of the first lumen to a fourth opening at a distal portion of a radially-outer surface of the valve stem. The second lumen may be transverse to the first lumen, and fluidly connects the first lumen with an area exterior to the valve stem. The valve may further include a face seal at the fourth opening of the second lumen. The face seal may be annular and may be configured to form a slidable interference fit with a wall of the medical device so that a fluid is prevented from flowing between an area outside of the radially outer portion of the face seal and the fourth opening. The valve may also include an air seal coupled to a radially-outer surface of the valve stem. The air seal may be configured to align with a second fluid inlet of the medical device when the valve is in the second position. The first lumen may include a bend proximate to the proximal opening. The face seal and the air seal may be longitudinally-aligned on a radially-outer surface of the valve stem. A proximal portion of the first lumen may be parallel and longitudinally aligned with the second lumen.

In other aspects of the present disclosure, the valve may include one or more of the features below. The valve may further include one or more threads protruding from a proximal portion of the exterior surface of the valve stem, and wherein, when each of the at least one thread are received by at least one groove of the medical device, the first opening may be configured to align with the fluid outlet, the fourth opening may be configured to align with the first fluid inlet, the air seal may be configured to align with the second fluid inlet, and the valve may be configured to be in the second position. The plurality of seals may include a first seal, a second seal, a third seal, and a fourth seal. The first seal may be positioned proximal to the first opening; the second seal may be positioned distal to the first opening; the third seal may be positioned distal to the second seal and proximal to the fourth opening; and the fourth seal may be positioned distal to the fourth opening and proximal to the second opening. Each of the first seal, the second seal, the third seal, and the fourth seal may be positioned within a first recess, a second recess, a third recess, and a fourth recess, respectively. Each of the first recess, the second recess, the third recess, and the fourth recess may be in the exterior surface of the valve stem and extend circumferentially about the longitudinal axis of the valve stem.

In other aspects of the present disclosure, a method of delivering liquid to an air outlet of a medical device, the medical device including an air inlet, the air outlet, a liquid inlet, and a liquid outlet. The method may include moving a first seal of a valve distally relative to the air inlet, the air outlet, the liquid inlet, and the liquid outlet from proximal to the air outlet to distal to the air outlet. The method may also include moving a first opening of a lumen extending through the valve from out of alignment with the air outlet to in alignment with the air outlet. The first opening may be at a proximal portion of a radially-outer surface of the valve. The method may further include applying liquid to the liquid inlet; and delivering the liquid to the air outlet via a second opening in the valve and the first opening in the valve.

In other aspects, the method of delivering liquid to an air outlet of a medical device may further include one or more of the features below. The method may further include, via a stem, opening a channel seal positioned at the second opening to permit a flow of fluid through the second opening and fluidly connect the liquid inlet, the air outlet, and the lumen. The lumen may be a first lumen, and the method may further including moving a face seal at a third opening of a second lumen of the valve from out of alignment with the fluid inlet to in alignment with the fluid inlet; and moving an air seal coupled to a radially-outer surface of the valve from out of alignment with the air inlet to in alignment with the air inlet, wherein the air seal prevents air flow from the air inlet into a valve cylinder of the medical device; so that the liquid inlet, the air outlet, the first lumen, and the second lumen are fluidly connected. The method may further include rotating the valve about a central longitudinal axis of the valve. The method may also include moving a third seal of the valve distally relative to the air inlet, the air outlet, the liquid inlet, and the liquid outlet from proximal to the fluid outlet to distal to the fluid outlet and proximal to the fluid inlet; and moving a fourth seal of the valve distally relative to the air inlet, the air outlet, the liquid inlet, and the liquid outlet from proximal to the fluid outlet to distal to the fluid outlet and proximal to the fluid inlet.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to a surface (e.g., a button) contacted by an operator for operating a valve, and the term "distal" means a direction away from the surface (e.g., a button) for operating the valve. Proximal and distal directions are labeled with arrows marked "P" and "D", respectively, throughout the figures. Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

A valve may be configured to provide cleaning functionality to air channels of an endoscope. In at least some embodiments, the valve may be appropriate for a single-use and therefore be disposable, and in other embodiments, the valve may be appropriate for repeated use. In a first configuration, the valve may provide a continuous feed of air to an air channel in a handle and sheath of an endoscope, and through an air/water nozzle at the distal end of the endoscope. In a second configuration, the valve may feed water into the air channel in the handle and sheath and through an air/water nozzle. In some examples, the valve may be made from a limited number of parts and materials, to limit its cost, so that it is disposable.

Figure 1A:
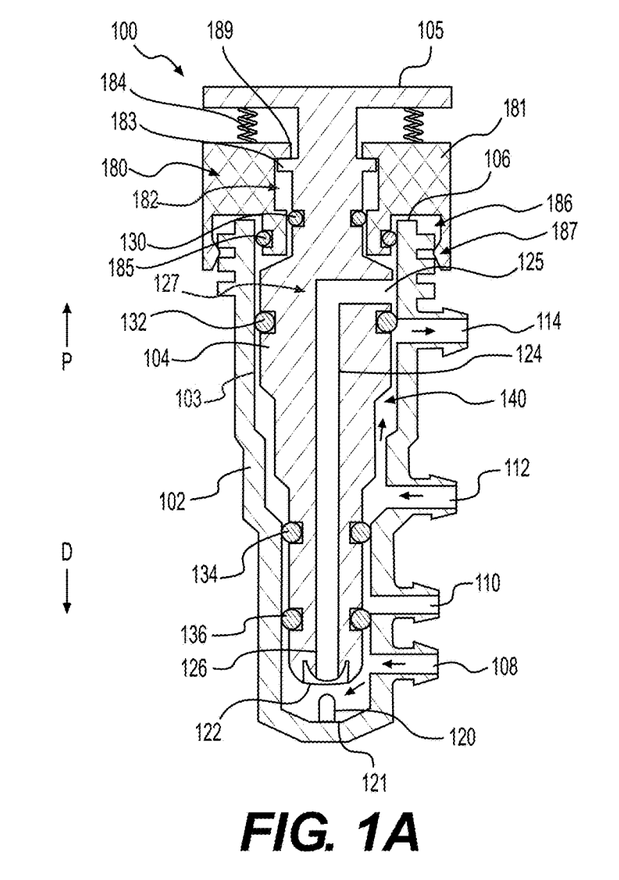
FIGS. 1A-1B show cross-sectional views of a first exemplary valve.

FIG. 1 shows a cross-sectional view of an exemplary valve 100 in a valve cylinder 102. Valve cylinder 102 may have surfaces 103 that define a cavity into which valve 100 may be inserted. Valve cylinder 102 may include connections to channels for inflow or outflow of air or water in a medical device, such as an endoscope. For example, valve cylinder 102 may have an air inlet 112 and an air outlet 114. Valve cylinder 102 may also have a water inlet 108 and a water outlet 110. From proximal to distal, the outlets may be ordered as follows: air outlet 114, air inlet 112, water outlet 110, and water inlet 108. Valve cylinder 102 may be incorporated in a handle of the medical device, for example an endoscope.

Valve 100 may have a valve stem 104. Valve stem 104 may be cylindrical and may have a decreasing circumference around a longitudinal axis of valve stem 104 moving from a proximal portion to a distal portion of the valve stem 104. Valve stem 104 may have an exterior surface configured to align with an interior surface 103 of valve cylinder 102. Portions of valve stem 104 may be made from metal (e.g., stainless steel, titanium, aluminum, etc.), from a polymer (e.g. polycarbonate, ABS, HDPE, Nylon, PEEK, thermoplastic, plastic, etc.), or from any other suitable material, or combinations thereof.

Valve stem 104 may include a channel 124 extending from a distal end of valve stem 104 to a proximal portion of valve stem 104. Channel 124 may include a proximal opening 125, a distal opening 126, and a turn or bend 127. Channel 124 may fluidly connect an opening in a channel seal 122 to an area at a proximal portion of valve cylinder 102 external to valve stem 104. Turn 127 may be a substantially ninety degree turn such that proximal opening 125 faces radially outward from a central longitudinal axis of valve stem 104 and distal opening 126 faces the direction of the central longitudinal axis of valve stem 104. In some examples, turn 127 may be a curved portion of channel 124 (not shown).

Proximal portion of valve 100 may include a button 105 and an actuation mechanism 180. Actuation mechanism 180 may be positioned between button 105 and valve cylinder 102. Button 105 may be formed as one continuous structure with valve stem 104, or button 105 may be a separate structure attached to valve stem 104. Button 105 may have an outer circumference that is wider than a proximal opening 106 of valve cylinder 102, so that when button 105 is depressed, button 105 cannot pass through the proximal opening of valve cylinder 102. In some examples, button 105 may have an outer circumference that is narrower than a proximal opening 106 of valve cylinder 102, and actuation mechanism 180 may prevent button 105 from passing through the proximal opening of valve cylinder 102.

Valve stem 104 may be fitted with one or more seals. For example, valve stem 104 may include, in a direction from proximal to distal, a first seal 130, a second seal 132, a third seal 134, and a fourth seal 136. Seals 130, 132, 134, 136 may be, for example, O-rings. Seals 130, 132, 134, 136 may be formed from an elastomeric material. Valve stem 104 may also include a channel seal 122, which may be made of the same or different material as seals 130, 132, 134, 136 (e.g., an elastomeric material), or any material to form a seal between the valve stem 104 and the valve cylinder 102 to prevent a fluid flow. Channel seal 122 may prevent passage of fluid or other substance into channel 124 when in a closed position, and may permit passage of fluid or other substances proximally past channel seal 122 when in an open position. Channel seal 122 may be opened by a channel stem 120 positioned at a distal inner surface 121 of valve cylinder 102. First seal 130 and second seal 132 may be disposed on a proximal portion of valve stem 104. Third seal 134 and fourth seal 136 may be disposed on a distal portion of valve stem 104. Channel seal 122 may be disposed at a distal end of valve stem 104. Alternatively, seals 130, 132, 134, 136 and channel seal 122 may be disposed on alternative portions of valve stem 102 or in different orders. Proximal opening 125 of channel 124 may be disposed between first seal 130 and second seal 132. Channel seal 122 may be disposed at distal opening 126 of channel 124 and close opening 126 when seal 122 is in a closed position.

Seals 132, 134, 136 may be configured so as to form a slidable interference fit between seals 132, 134, and 136 and surface 103. Thus, valve stem 104 can move relative to surface 103, but fluids (e.g. water and air) cannot move between seals 130, 132, 134, and 136 and surface 103. Thus, seals 132, 134, and 136 prevent movement of fluids in a proximal or distal direction past seals 132, 134, and 136.

Channel seal 122 may be biased toward a closed position such that fluid is prevented from flowing through channel seal 122 when channel seal 122 is in a closed position. Channel seal 122 may be opened by positioning an object within a radially-inner portion of channel seal 122. Channel seal 122 may be, for example, a circular and plate-like shape with a slit, flap, or duck-bill seal at its radially-inner portion. Channel seal 122 may be configured to receive channel stem 120. For example, stem 120 may protrude through a portion of a slit, flap, or other portion of seal 122. Channel stem 120 may protrude from a distal inner surface 121 of valve cylinder 102. Channel stem 120 may be cylindrical and may have a circumference smaller than the circumference of channel 124. Distal opening 126 of channel 124 may be configured to received channel stem 120. In some embodiments not shown, channel stem 120 may include a channel, lumen, or other configuration to allow fluid to move through an interior portion of channel stem 120 from an area proximate to a distal portion of channel stem 120 to an area proximal to channel stem 120. Channel stem 120 may have a rounded or pointed proximal end configured to be pushed through channel seal 122. Channel stem 120 may be resilient enough to maintain its shape when channel seal 122 contacts channel stem 120. When valve 100 is translated distally towards distal interior surface 121 of valve cylinder 102, channel seal 122 may move from a closed position to an open position once channel stem 120 is positioned within distal opening 126 of channel 124. When channel stem 120 is positioned within distal opening 126, channel seal 122 may be opened and fluid may flow around channel stem 120 and channel seal 122 into channel 124. Channel stem 120 may be rigid, metal, plastic, or other suitable material. In some examples, channel stem 120 may be incorporated into valve cylinder 102. In some examples, channel stem 120 may be cylindrical.

Valve 100 may also include an actuation mechanism 180. Actuation mechanism 180 may include a biasing member, such as spring 184, that biases valve 100 towards a first configuration shown in FIG. 1A. In some examples, spring 184 may be positioned around the longitudinal axis of valve 100 and may have a helical shape that wraps around a proximal portion of valve 100 distal to button 105. In other examples, spring 184 may be a plurality of springs positioned between button 105 and collar 181. When a user presses on button 105, button 105 may compress a spring of actuation mechanism 180, and valve stem 104 may translate distally. In some examples, when a user releases the user's finger from button 105, valve 100 returns to the first configuration shown in FIG. 1A. In other examples, actuation mechanism 180 may provide a bistable system where in one stable position the valve 100 is retracted from the distal surface 121 of valve cylinder 102, and in the other stable position valve 100 is extended such that a distal portion of valve stem 104 contacts distal surface 121 and/or channel stem 120. In this latter position, valve 100 may include a locking mechanism to hold valve stem 104 in position. In some examples, actuation mechanism 180 may provide a means for a user to switch between operating configurations of valve 100.

Figure 1B:
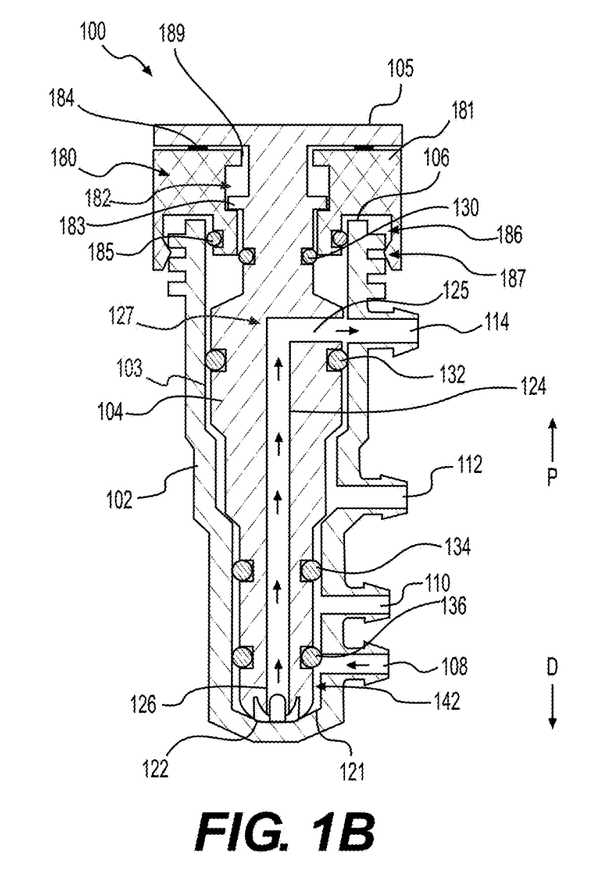

An exemplary actuation mechanism 180 is shown in FIGS. 1A and 1B. Actuation mechanism 180 may include a collar 181, a biasing member 184, a seal 185 positioned at a proximal portion of the collar 181, and a protrusion 183 extending from an exterior surface of valve 100.

Collar 181 may be annular and may include a lumen 189 sized to receive valve 100. Collar 181 may include an annular channel 186 at a distal portion of collar 181 configured to receive a proximal end of valve cylinder 102. Channel 186 may include a protrusion 187 that is configured to extend into a recess of valve cylinder 102 to form a snap-fit and couple collar 181 to valve cylinder 102. For example, channel 186 may receive an outer lip of valve cylinder 102 and protrusion 187 may extend within a recess of valve cylinder 102 to fixedly couple collar 181 to valve cylinder 102. A seal 185 may be positioned at a radially-inner portion of channel 186 and may be configured to form a slidable interference fit between seal 185 and surface 103 of valve cylinder 102. Seal 185 may have any of the characteristics previously described in relation to seals 132, 134, 136. When collar 181 is coupled to valve cylinder 102, seal 185 may prevent fluid from exiting valve cylinder 102.

Seal 130 of valve 100 may also have any of the characteristics previously described in relation to seals 132, 134, 136. When valve 100 is positioned within lumen 189 of collar, seal 130 may form a slidable interference fit between seal 130 and collar 181. Seal 130 may prevent fluid from exiting from valve cylinder 102 through lumen 189.

Figure 3:
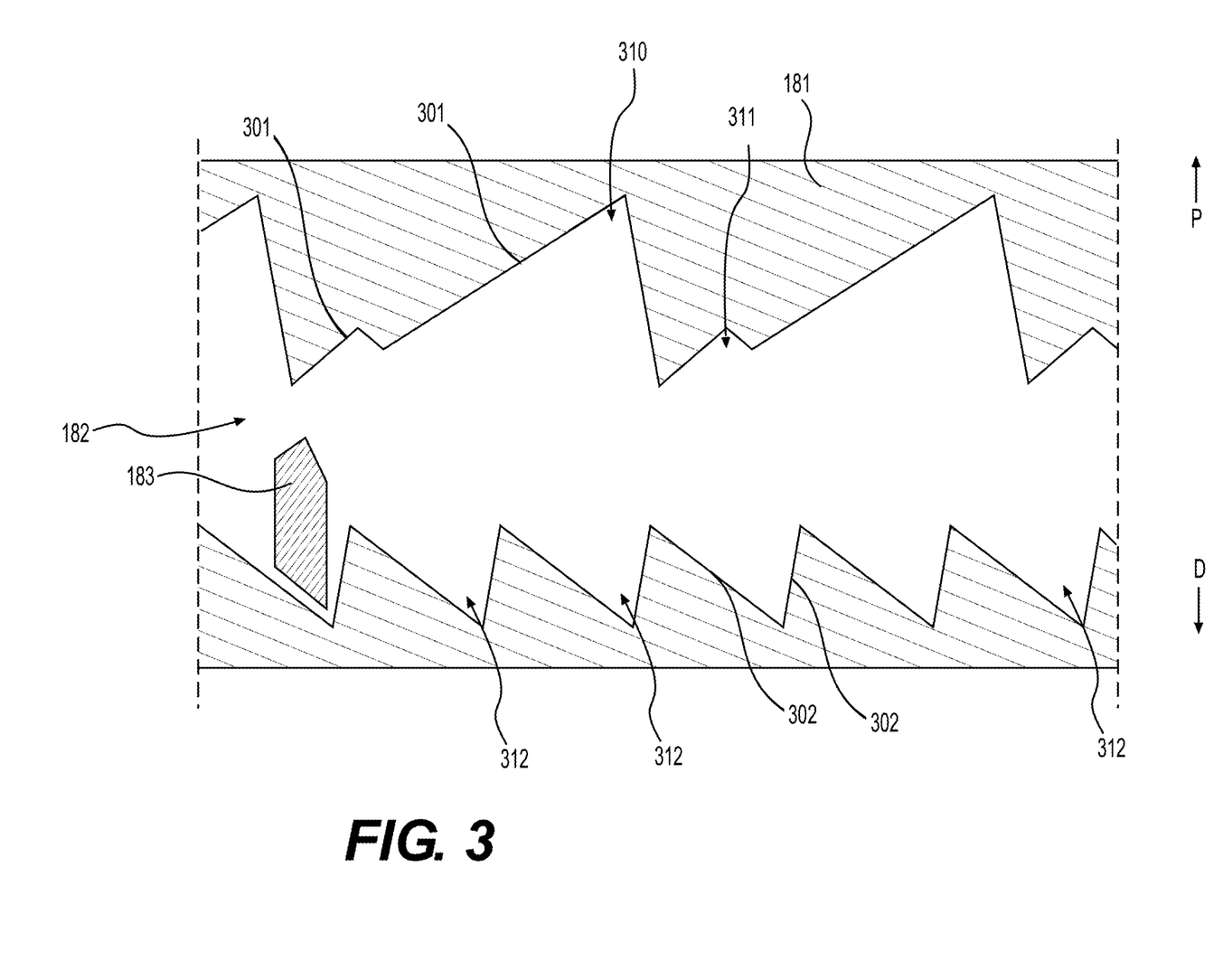
FIG. 3 shows a side cross-sectional view of a channel and a protrusion of the first exemplary valve shown in FIGS. 1A-1B.

Collar 181 may include a second channel 182 extending circumferentially about a central longitudinal axis of collar 181 and positioned at a radially-inner surface of collar 181. An exemplary embodiment of a side cross-sectional view of second channel 182 and protrusion 183 of valve 100 is shown in FIG. 3. Second channel 182 may be annular and may include proximal surfaces 301 and distal surfaces 302, each of which may be transverse to the longitudinal axis of collar 181. Channel 182 may be configured to receive protrusion 183 of valve 100. Surfaces 301 may be angled and configured to guide protrusion 183 between a first configuration (shown in FIG. 1A) and a second configuration (shown in FIG. 1B). Biasing member 184 may bias protrusion 183 towards the proximal direction such that when a user releases button 105, protrusion 183 will move proximally until protrusion 183 contacts one of proximal surfaces 301. Protrusion 183 may include exterior surfaces configured to mate with proximal surfaces 301 and distal surfaces 302 of second channel 182. As valve 100 is depressed, such as when a user presses on button 105 to move valve 100 distally, the proximal surfaces 301 may rotate valve 100 by the interaction between one or more of proximal surfaces 301 and protrusion 183 until protrusion 183 is positioned within an intermediate portion 312 in second channel 182 (such as shown in FIG. 3). In other examples, collar 181 will rotate about longitudinal axis of valve 100, due to forces applied by protrusion 183 on collar 181. Once protrusion 183 is positioned in an intermediate portion 312 and a user then releases button 105, protrusion 183 may be translated proximally via a force applied to valve 100 via biasing member 184, thus moving protrusion 183 from intermediate portion 312 to one of the locking features 310, 311 of second channel 182. For example, valve 100 may be in a first configuration shown in FIG. 1A when protrusion 183 is positioned at locking feature 310, and may be in a second configuration shown in FIG. 1B when protrusion 183 is positioned at locking feature 311. When a user presses down on button 105 and moves valve 100 distally, protrusion 183 may move to one of several intermediate portions 312, and then, when a user releases button 105, biasing member 184 may translate valve 100 proximally and position protrusion 183 at a locking feature 310, 311 that is adjacent to the locking feature 310, 311 in which protrusion 183 was previously positioned. Valve 100 may move circumferentially around collar 181 as a user transitions valve 100 between a first configuration (shown in FIG. 1A) and second configuration (shown in FIG. 1B), and protrusion 183 may slidably engage proximal surfaces 301 and/or distal surfaces 302 as valve 100 transitions between the first configuration (shown in FIG. 1A) and second configuration (shown in FIG. 1B), for example as protrusion 183 moves between locking features 310, 311. Alternatively, collar 181 may move circumferentially around the longitudinal axis of valve 100 and valve 100 may not rotate.

In some examples, valve 100 including button 105 may be rotatable relative to biasing member 184. In other examples, biasing member 184 may be fixedly coupled to valve 100 and may be rotatable relative to collar 181. In some examples, biasing member 184 may be in an expanded state when valve 100 is in a first configuration shown in FIG. 1A and may be in a compressed state when valve 100 is in a second configuration shown in FIG. 1B.

When actuation mechanism 180 provides a bistable system, valve 100 may be configured to move between a first stable configuration and a second stable configuration. In some examples, the user may press on button 105 to move valve 100 distally, compressing a biasing member, until actuation system 180 creates an audible "click" sound. Once the user hears the audible "click" sound, the user may release button 105 and valve 100 may be in and/or move to a second stable configuration that is distal relative to the first stable configuration. The audible "click" sound may be caused, in some examples, by the movement of protrusion 183 between locking features 310, 311 and intermediate portion 312 of second channel 182. To transition valve 100 from the second stable configuration to the first stable configuration, the user may press on button 105 to move valve 100 distally until actuation system 180 creates an audible "click" sound, and then the user may release button 105 and valve 100 may move proximally to the first stable configuration via a force supplied by the biasing member. In some examples, the first stable configuration may be the configuration shown in FIG. 1A and the second stable configuration may be the configuration shown in FIG. 1B.

FIG. 1A shows valve 100 in a first configuration. In the first configuration of valve 100, neither air nor water may be delivered to either the proximal opening 125 or distal opening 126 of channel 124. Air or other fluid may be delivered to an air channel of an endoscope via air inlet 112 and air outlet 114, but water or other fluid is not delivered to any channel of the endoscope from water inlet 108. Channel seal 122 is positioned proximal to channel stem 120, and thus channel seal 122 seals distal opening 126 and prevents passage of fluid through distal opening 126. Seal 136 prevents proximal fluid flow, such as fluid flow from water inlet 108 to water outlet port 110. Seal 134 prevents fluid flow, such as air flow, from air inlet 112 to water outlet 110. Seal 132 prevents fluid flow from air inlet 112 from flowing into proximal opening 125 of channel 124 and/or from exiting valve cylinder 102. Seal 130 prevents fluid flow from exiting valve cylinder 102 at the proximal end, and may serve as a back-up seal to seal 132 for preventing fluid flow from air inlet 112 from exiting valve cylinder 102. In this first configuration shown in FIG. 1A, air or other fluid may be supplied to air inlet 112 and may flow within an annular space 140 to outlet port 114 such that air inlet 112 is in fluid communication with air outlet 114. Thus, in the first configuration, air may flow through air inlet 112 and out of air outlet 114, and water may not flow to water outlet 110, channel 124, or air outlet 114. The arrows in FIG. 1A show this air flow path.

In the second configuration, shown in FIG. 1B, water is delivered to an air channel of the endoscope but air is not delivered to any endoscope channel. To transition from the first configuration to the second configuration, button 105 may be depressed. For example, button 105 may be depressed until a user hears an audible "click" sound created by actuation mechanism 180. In some examples, actuation mechanism 180 may cause tactile feedback to a user to indicate that valve 100 is in the second configuration.

In transitioning from the first configuration to the second configuration, valve stem 104 may translate distally relative to valve cylinder 102, as a result of button 105 being pressed downward. A force on button 105 to transition valve 100 from the first configuration to the second configuration may cause the distalmost end of valve stem 104, which may include channel seal 122, to contact channel stem 120. Once channel stem 120 contacts channel seal 122, channel seal 122 may open as valve 100 moves distally relative to valve cylinder 102 and channel stem 120 penetrates channel seal 122.

In the second configuration, channel seal 122 may be open and proximal opening 125 may be aligned with air outlet 114, such that water may flow from water inlet 108, through annular space 142, around channel stem 120, and into channel 124, to air outlet 114. Fourth seal 136 may be proximal to water inlet 108 and distal to water outlet 110. Thus, water from water inlet 108 may not move proximally past fourth seal 136 to water outlet 110, but may move through channel 124 and air outlet 114 to flush an air channel of an endoscope. Third seal 134 may be proximal of water outlet 110 and distal to air inlet 112. Second seal 132 may be proximal to air inlet 112 and distal to air outlet 114, thus preventing air flow from air inlet 112 to air outlet 114. Also, second seal 132 may prevent water flow from proximal opening 125 from entering air inlet 112. First seal 130 may be proximal to air outlet 114 and distal to proximal opening 106, and thus may prevent water flow from proximal opening 125 from exiting valve cylinder 102. As a result, in the second configuration, the only fluid flow to the endoscope sheath is that of water through the air channel. The second configuration of valve 100 may provide a means for a user to flush the air channel of an endoscope with water.

In order to make use of valve 100, an operator may insert valve 100 into valve cylinder 102 of an endoscope. For example, following an endoscopic procedure, the endoscope may be removed from the patient for reprocessing, a valve used during the endoscope procedure may be removed, and valve 100 may be inserted into valve cylinder 102. Valve 100 may be inserted into valve cylinder 102 by pressing valve 100 into valve cylinder 102. In some examples, valve 100 may be rotatable by the user to a selected position, e.g., a keying feature in order to rotate valve 100 into the correct position within valve cylinder 102. The user may first apply air flow to air inlet 112 to allow air to flow through annular space 140 to air outlet 114. Also, user may then transition valve 100 from a first configuration (shown in FIG. 1A) to a second configuration (shown in FIG. 1B). Specifically, button 105 may be fully depressed so that valve 100 transitions to the second configuration (shown in FIG. 1B). Valve 100 may flush water through the air channel. After flushing is complete, a user may release button 105 to stop water flow to air outlet 114. In other examples, a user may press button 105 until an actuation mechanism 180 creates a "click" sound. Then the user may then release button 105 and actuation mechanism 180 may transition valve 100 from the second configuration to the first configuration via a biasing member, and thus stop water flow to air outlet 114. After flushing of the air channel is complete, valve 100 may be removed from valve cylinder 102. Valve 100 may be removed from valve cylinder 102 by grasping the exposed portion of the proximal end of valve 100 and pulling proximally to remove valve 100 from valve cylinder 102. Once removed from valve cylinder 102, in some examples valve 100 would be disposed.

Figure 2A:
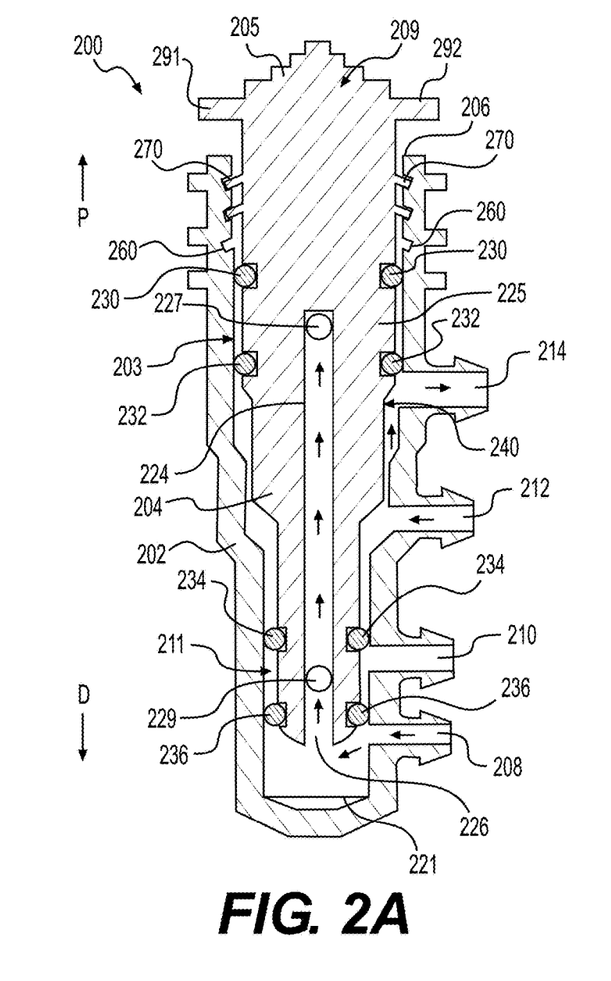
FIGS. 2A-2B show cross-sectional views of a second exemplary valve.
Figure 2B:
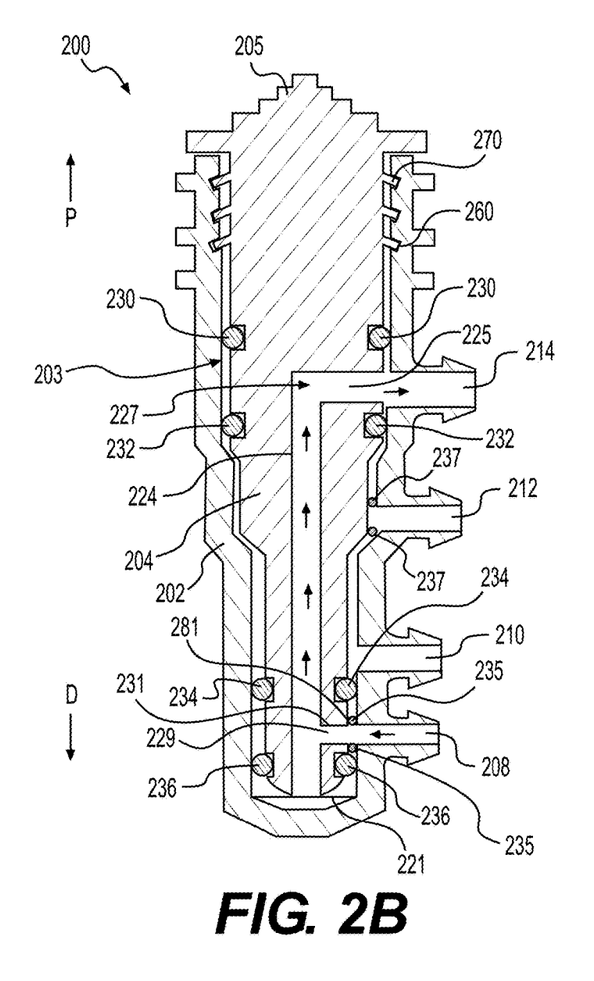

FIGS. 2A and 2B depict configurations of another exemplary valve 200 within a valve cylinder 202. FIG. 2A shows valve 200 in a first configuration, and FIG. 2B shows valve 200 in a second configuration. Valve 200 may have a valve stem 204. Valve stem 204 may be substantially cylindrical extending along a longitudinal axis and may have a proximal end 209 and a distal end 211. Proximal end 209 of valve stem 204 may include a button 205, which may be configured to be contacted by one or more fingers of a user in operation of valve 200. External screw/threads 270 may protrude radially from a proximal portion of valve stem 204 and may be configured to be received by thread grooves 260 in valve cylinder 202. When valve 200 is inserted into valve cylinder 202, threads 270 may engage grooves 260 and a user may rotate button 205 in order to couple valve 200 to valve cylinder 202.

Valve stem 204 may include a channel 224 extending proximally from distal end 211 of valve stem 204 to a proximal portion of valve stem 204. Channel 224 may include a proximal opening 225, a distal opening 226, a bend or turn 227, and a side opening 229. Turn 227 may be an approximately ninety degree turn such that proximal opening 225 faces radially outward from a central longitudinal axis of valve stem 204 and distal opening 226 faces the direction of the central longitudinal axis of valve stem 204. Proximal opening 225 may be configured to align with air outlet 214 when valve 200 is fully inserted within valve cylinder 202 (shown in FIG. 2B). In some examples, turn 227 may be a curved portion of channel 224 (not shown). Side opening 229 may be positioned at a distal portion of channel 224 and may connect a side channel 231 (shown in FIG. 2B) to channel 224. Side channel 231 may extend in a direction radially outward from the central longitudinal axis of valve stem 204 and may be transverse to channel 224. In some examples, side channel 231 may be perpendicular to channel 224. Side channel 231 may fluidly connect channel 224 to an area at a distal portion of valve cylinder 202 external to valve stem 204. Side channel 231 may be configured to align with water inlet 208 when valve 200 is fully inserted within valve cylinder 202 (shown in FIG. 2B). Channel 224 may fluidly connect an area at a distal portion of valve cylinder 202 external to valve stem 204 to an area at a proximal portion of valve cylinder 202 external to valve stem 204.

Valve stem 204 may also be fitted with a plurality of seals. For example, valve stem 204 may include a first seal 230, a second seal 232, a third seal 234, and a fourth seal 236. Seals 230, 232, 234, and 236 may be disposed in grooves of valve stem 204. Seals 230, 232, 234, and 236 may have any of the properties of seals 130, 132, 134, or 136, described above. Seals 230, 232, 234, and 236 may have a slidable interference fit with a surface 203 of valve cylinder 202 so that fluids (e.g., air, water) cannot move proximally or distally between seal 230, 232, 234, or 236 and the surface 203 of valve cylinder 202. First seal 230 may be disposed proximally of proximal opening 225 of channel 224 and may be disposed distally of threads 270. Second seal 232 may be disposed distally of proximal opening 225 of channel 224 and proximally of third seal 234. Third seal 234 may be disposed distally of second seal 232 and proximally of side channel 231. Fourth seal 236 may be disposed distally of side channel 231 and proximally of distal opening 226 of channel 224.

Valve stem 204 may also include a face seal 235 positioned at the outlet 281 of side channel 231 and coupled to the radially outer surface of valve stem 204 (see FIG. 2B). Face seal 235 may be annular and may be configured to surround the outlet 281. Face seal 235 may have any of the properties of seals 130, 132, 134, 136, 230, 232, 234, and 236. Face seal 235 may have a slidable interference fit with a surface 203 of valve cylinder 202 so that fluids (e.g., air, water) cannot move between the outlet 281 and the area external to the radially-outer surface of face seal 235. Face seal 235 may be configured to allow fluid flow between water inlet 208 and side channel 231 when outlet 281 is aligned with water inlet 208. When inlet 208 is not overlapping with outlet 281 (such as the configuration shown in FIG. 2A), face seal 235 may prevent flow of fluid from side channel 231 into an area outside the radially-outer surface of face seal 235 within valve cylinder 202.

Valve stem 204 may further include a second face seal 237 or static seal coupled to an exterior surface of valve 200 between the second seal 232 and third seal 234. Second face seal 237 may have any of the features described above with regard to face seal 235. Second face seal 237 may be positioned such that when valve 200 is completely inserted within valve cylinder 202 (shown in FIG. 2B), second face seal 237 aligns with air inlet 212. When second face seal is aligned with air inlet 212, second face seal 237 may prevent fluid flow between air inlet 212 and the interior portion of valve cylinder 202 outside the radially-outer surface of second face seal 237. In some examples, second face seal 237 may be circular and disc-shaped (without a radially-inner opening) to completely cover inlet 212 and may prevent the flow of fluid into the interior portion of valve cylinder 202 when aligned with air inlet 212. By preventing or blocking fluid flow into the interior portion of valve cylinder 202, second face seal 237 may prevent complications associated with air flow within valve cylinder 202 while flushing an air channel of an endoscope with water, among other potential benefits.

Valve stem 204 may also include one or more threads 270. Threads 270 may be on a circumferential outer surface of valve stem 204 and positioned proximal to button 205. Threads 270 may couple valve 200 to valve cylinder 202 when positioned within one or more grooves 260 at a proximal portion of the interior surface 203 of valve cylinder 202. In some examples, one or more threads 270 may be configured to couple valve 200 to valve cylinder 202 by a user rotating valve 200 ninety degrees. In some examples, a user may insert valve 200 into valve cylinder 202 and rotate valve 200 ninety degrees to position valve 200 within valve cylinder 202 in the configuration shown in FIG. 2B. In other examples, threads may be configured to rotate one hundred and eighty degrees, two hundred and seventy degrees, three hundred and sixty degrees, or any other amount of rotation to position threads 270 within grooves 260 and achieve the valve configuration shown in FIG. 2B. In some examples, valve 200 may transition between the configuration shown in FIG. 2A and the configuration shown in FIG. 2B by a user rotating button 205 ninety degrees. In some examples, valve 200 may transition between the configuration shown in FIG. 2A and the configuration shown in FIG. 2B by a user pressing on button 205 and rotating valve 200 simultaneously.

FIG. 2A shows valve 200 in a first configuration. In the first configuration, air may be delivered to an air channel of an endoscope via air inlet 212 and air outlet 214, but water is not delivered to water outlet 210 or air outlet 214. Seal 236 prevents proximal fluid flow, such as fluid flow from water inlet 208 to water outlet 210. Seal 234 prevents fluid flow, such as air flow, from air inlet 212 to water outlet 210. Water or other fluid may flow from water inlet 208 through channel 224 to proximal opening 225. Seal 232 prevents fluid flow from air inlet 212 from flowing into proximal opening 225, and prevents fluid flow from proximal opening 225 to air outlet 214 and air inlet 212. Seal 230 prevents fluid flow from exiting valve cylinder 202, and prevents fluid flow from proximal opening 225 from exiting valve cylinder 202. Face seal 235 prevents fluid flow between side channel opening 281 and the exterior portion of valve stem 204 between seals 234 and 236. In this first configuration shown in FIG. 2A, air or other fluid may be supplied to air inlet 212 and may flow within annular space 240 to air outlet 214 such that air inlet 212 is in fluid communication with air outlet 214. Thus, in the first configuration, air may flow through air inlet 212 and out of air outlet 214, and water may not flow to water outlet 210 or air outlet 214.

In the second configuration, shown in FIG. 2B, water or other fluid from water inlet 208 is delivered to an air channel of the endoscope, but air or other fluid from air inlet 212 is not delivered to any endoscope channel. To transition from the first configuration to the second configuration, button 205 may be twisted/rotated. For example, button 205 may be rotated until at least one radially-outer portion or flange 291, 292 is flush or proximate to opening 206 of valve cylinder 202. In some examples, distal end 211 of valve 200 may contact distal surface 221 of valve cylinder 202 when in the second configuration.

In the second configuration, proximal opening 225 of channel 224 may be aligned with air outlet 214, and side channel 231 may be aligned with water inlet 208, such that water may flow from water inlet 208, through side channel 231 and channel 224, to air outlet 214. Fourth seal 236 may be distal to water inlet 208. Third seal 234 may be proximal to water inlet 208 and distal to water outlet 210. Face seal 235 may be positioned around water inlet 208 and side channel opening 281, such that fluid flowing between water inlet 208 and side channel 231 does not flow to an area external to valve 200 within valve cylinder 202 exterior to face seal 235. Channel 224 allows fluid to flow out of distal opening 226 to a distal portion of valve cylinder 202. Seal 236 prevents fluid flowing out of distal opening 226 from flowing proximally beyond seal 236. Second face seal 237 may be aligned with air inlet 212 and may prevent the flow of fluid (such as air) into an interior portion of valve cylinder 202. Second seal 232 may be distal to air outlet 214 and proximal to air inlet 212, and may prevent fluid flow between proximal opening 225 and air inlet 212. First seal 230 may be proximal to air outlet 214 and distal to opening 206 of valve cylinder 202, and may prevent fluid flow between proximal opening 225 and the exterior of valve cylinder 202. Thus, water may move through water inlet 208, side channel 231, channel 224, and air outlet 214 to flush an air channel of an endoscope. As a result, in the second configuration, the only fluid flow to the endoscope sheath is that of water through the air channel. The second configuration of valve 200 may provide a means for a user to flush the air channel of an endoscope with water.

In order to make use of valve 200, an operator may insert valve 200 into valve cylinder 202 of an endoscope. For example, following an endoscopic procedure, the endoscope may be removed from the patient for reprocessing, a valve used during the endoscope procedure may be removed, and valve 200 may be inserted into valve cylinder 202. Button 105 may be rotated so that valve 200 transitions to the second configuration (shown in FIG. 2B). Valve 200 may flush water through the air channel. After flushing is complete, a user may rotate button 205 to stop water flow to air outlet 114. In some examples, valve 200 may be configured to transition from the configuration shown in FIG. 2A to the configuration shown in FIG. 2B when a user rotates valve 200 a predetermined degree of rotation, and the predetermined degree of rotation may be between 60 degrees and 270 degrees. In some examples, a user may rotate button 205 to align valve 200 in the first configuration of FIG. 2A to allow flow of air into air outlet 214, and thus allow air flow into an air channel of an endoscope. After flushing and/or air flow application is complete, a user could either move button 205 to disable the flow of water or air or could simply remove valve 200 from valve cylinder 202 by continually rotating button 205 (such that one or more threads 270 translate out of grooves 260) and pulling proximally on valve 200. The endoscope would be subject to further processing, and, in some examples, valve 200 may be disposed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising:
   a valve;
   a protrusion extending outward from the valve; and
   an actuation mechanism, the actuation mechanism comprising:
      a collar, the collar including a channel extending about a longitudinal axis of the collar, wherein the channel includes a plurality of angled surfaces disposed transverse to the longitudinal axis of the collar, wherein the plurality of angled surfaces includes a plurality of proximal surfaces and a plurality of distal surfaces disposed opposite the plurality of proximal surfaces; and
      a biasing member configured to bias the protrusion in a proximal direction, wherein interaction between one or more of the plurality of proximal surfaces and the protrusion rotates the valve, wherein, upon positioning of the protrusion in at least one of a plurality of intermediate portions of the channel, the valve stops its rotational movement;
   wherein the protrusion is received within the channel, wherein the protrusion is configured to translate from a first position within the channel to a second position within the channel, and wherein, upon translation of the protrusion from the first position to the second position, the collar rotates about a longitudinal axis of the valve.

2. The medical device of claim 1, wherein an angle of a proximalmost surface of the protrusion, with respect to the longitudinal axis of the collar, is equal to an angle of each of the plurality of proximal surfaces, with respect to the longitudinal axis of the collar.

3. The medical device of claim 2, wherein an angle of a distalmost surface of the protrusion, with respect to the longitudinal axis of the collar, is equal to an angle of each of the plurality of distal surfaces, with respect to the longitudinal axis of the collar.

4. The medical device of claim 3, wherein each of the plurality of angled surfaces is configured to guide the protrusion between the first position and the second position, wherein at least one angled surface of the plurality of angled surfaces includes a locking feature.

5. The medical device of claim 4, wherein the biasing member is configured to translate the protrusion from the first position within the channel to the second position within the channel upon engagement of the biasing member, wherein the second position is a locking position.

6. The medical device of claim 5, wherein force applied to the collar by the biasing member moves the protrusion from an intermediate portion of the plurality of intermediate portions to the locking feature.

7. The medical device of claim 6, wherein the locking feature is a first locking feature, wherein, in a first configuration of the valve, the protrusion is positioned at the first locking feature, and wherein, in a second configuration of the valve, the protrusion is positioned at a second locking feature.

8. The medical device of claim 7, wherein the biasing member biases the protrusion through the plurality of intermediate portions, wherein the valve moves circumferentially around the collar as the valve transitions between the first configuration and the second configuration.

9. A medical device, comprising:
   a valve including a protrusion; and
   a collar disposed around the valve, the collar including a channel extending about a longitudinal axis of the collar, wherein the channel includes a plurality of surfaces disposed transverse to the longitudinal axis of the collar, and wherein the plurality of surfaces includes a plurality of proximal surfaces and a plurality of distal surfaces disposed opposite the plurality of proximal surfaces;
   wherein interaction between one or more of the plurality of proximal surfaces and the protrusion rotates the valve, wherein the channel includes a plurality of intermediate portions, wherein the protrusion being positioned in one of the plurality of intermediate portions stops rotational movement of the valve.

10. The medical device of claim 9, wherein the protrusion is configured to translate from a first position within the channel to a second position within the channel and wherein the collar is configured to rotate about the longitudinal axis as the protrusion translates from the first position to the second position.

11. The medical device of claim 9, wherein the protrusion is biased through the plurality of intermediate portions.

12. The medical device of claim 11, wherein the protrusion is biased from the plurality of intermediate portions to a locking feature.

13. A method for actuating a valve of a medical device, the medical device including: (a) a collar disposed around the valve, the collar including a channel extending about a longitudinal axis of the collar; and (b) a protrusion extending from an exterior surface of the valve and received within the channel, the method comprising:
  translating the protrusion from a first position within the channel to a second position within the channel,
  wherein translating the protrusion from the first position to the second position causes rotation of the collar about a longitudinal axis of the valve, and
  wherein translating the protrusion from the first position within the channel to the second position within the channel includes moving the protrusion to at least an intermediate portion of the channel.

14. The method of claim 13, wherein the channel includes a plurality of angled surfaces disposed transverse to the longitudinal axis of the collar, wherein the plurality of angled surfaces includes a plurality of proximal surfaces.

15. The method of claim 14, wherein each of the plurality of angled surfaces is configured to guide the protrusion between the first position and the second position.

\* \* \* \* \*